(12) United States Patent
Lee et al.

(10) Patent No.: US 8,650,936 B2
(45) Date of Patent: Feb. 18, 2014

(54) LIQUID CHROMATOGRAPHY DEVICE

(75) Inventors: Sang-Won Lee, Seoul (KR); Min-Sik Kim, Seoul (KR); Seok-Won Hyung, Seoul (KR)

(73) Assignee: Korea University Research and Business Foundation, Seoul (KR)

( * ) Notice: Subject to any disclaimer, the term of this patent is extended or adjusted under 35 U.S.C. 154(b) by 311 days.

(21) Appl. No.: 13/180,436

(22) Filed: Jul. 11, 2011

(65) Prior Publication Data

US 2013/0014568 A1    Jan. 17, 2013

(51) Int. Cl.
*G01N 1/00*    (2006.01)
(52) U.S. Cl.
USPC ....... 73/61.56; 73/61.52; 73/61.55; 73/61.58; 73/61.59; 210/198.2
(58) Field of Classification Search
USPC ............ 73/61.52, 61.55, 61.56, 61.58, 61.59; 210/198.2
See application file for complete search history.

(56) References Cited

U.S. PATENT DOCUMENTS

| | | | | |
|---|---|---|---|---|
| 5,234,599 | A * | 8/1993 | Cortes et al. | 210/659 |
| 6,086,767 | A * | 7/2000 | Walters et al. | 210/634 |
| 6,652,745 | B2 * | 11/2003 | Gjerde et al. | 210/198.2 |
| 7,637,147 | B2 * | 12/2009 | Lee et al. | 73/61.56 |
| 7,905,133 | B2 * | 3/2011 | Chordia et al. | 73/61.56 |
| 2006/0186028 | A1 * | 8/2006 | Hughes | 210/198.2 |
| 2012/0145617 | A1 * | 6/2012 | Lee et al. | 210/198.2 |

OTHER PUBLICATIONS

Link, A. J., Eng, J., Schieltz, D. M., Carmack, E., et al., 1999, "Direct Analyis of Protein Complexes Using Mass Spectrometry", Nat. Biotechnol., vol. 17, pp. 676-682.

Chen E. I., Newel J., Felding-Habermann B., Yates J. R. III, 2006, "Large Scale Protein Profiling by Combination of Protein Fractionation and Multidimensional Protein Indentification Technology (MudPIT)", Mol. Cell. Proteomics, vol. 5, pp. 53-56.

Kim, M.-S., Choie, W.-S., Shin, Y. S., Yu, M. H., Lee, S.-W., 2004, "Development of Ultra-High Pressure Capillary Reverse-Phase Liquid Chromatography/Tandem Mass Spectrometry for High-Sensitive and High-Throughput Proteomics", Bull. Korean Chem. Soc., vol. 25, pp. 1833-1839.

Shen, Y., Moore, R. J., Zhao, R., Blonder, J., et al., 2003, "High-Efficiency On-Line Solid-Phase Extraction Coupling to 15-150-m-i. d. Column Liquid Chromatography for Proteomic Analysis", Anal. Chem., vol. 75, pp. 3596-3605.

Shen Y., Tolic N., Masselon C., Pasa-Tolic L. et al., 2004, "Ultrasensitive Proteomics Using High-Efficiency On-Line Micro-SPE-NanoLC-NanoESI MS and MS/MS", Anal. Chem., vol. 76, pp. 144-154.

Shen Y., Smith R. D., Unger K. K., Kumar D., Lubda D., 2005, "Ultrahigh-Throughput Proteomics Using Fast RPLC Separations with ESI-MS/MS", Anal. Chem., vol. 77, pp. 6692-6701.

* cited by examiner

*Primary Examiner* — Hezron E Williams
*Assistant Examiner* — Hoang Nguyen
(74) *Attorney, Agent, or Firm* — Knobbe Martens Olson & Bear LLP

(57) ABSTRACT

A liquid chromatography device includes a sample inlet valve to which a sample to be analyzed is introduced, and a trap valve fluid-communicating with a solid phase extraction column and a reverse phase liquid chromatography column. The device further includes a solvent dividing unit dividing flow of a solvent discharged from the sample inlet valve into the first solvent inlet port and the second solvent inlet port of the trap valve. The liquid chromatography device improves resolution and increases reproducibility by allowing the sample injecting direction and the sample eluting direction to be opposite to each other.

13 Claims, 4 Drawing Sheets

LIQUID CHROMATOGRAPHY DEVICE

TECHNICAL FIELD

The following disclosure relates to a liquid chromatography device. More particularly, the following disclosure relates to a liquid chromatography device that has a simple configuration by using specialized cooperation between a T-shaped solvent dividing unit and a trap valve provided with a Z-shaped solvent flow path to modify the flow of a solvent, and improves the resolution by allowing the sample injecting direction and the sample eluting direction to be opposite to each other.

BACKGROUND

On-line solid phase extraction/capillary reverse phase liquid chromatography has been regarded as a very important technological system in studying proteomes by virtue of its high efficiency in analysis. Particularly, this allows effective separation of trace amounts of biological substances and enables highly efficient identification of trace amounts of proteins due to its broad spectrum of analyte-solid phase reactions.

As a method for analyzing proteins, a mass spectrometry-based method has served as a standard analytic platform of proteome study. A typical example of the method, such as a shot-gun method or a bottom-up method, includes hydrolysis of proteins into peptides prior to the analysis using a mass spectrometer. Such hydrolysis increases the solubility of biological samples and produces peptide digests that may be ionized and detected easily in a mass spectrometer.

However, the above-mentioned method inevitably causes complexity of samples. For example, in the case of one of the simplest proteomes, yeast proteome, 300,000 or more peptide fragments are produced from about 6,000 diverse proteins. Therefore, in order to solve the complexity of samples, various methods including on-/off-line multidimensional protein identification technology have been developed (Link, A. J., Eng, J., Schieltz, D. M., Carmack, E., et al., *Nat. Biotechnol.* 1999, 17, 676-682; Chen, E. I., Newel, J., Felding-Habermann, B., Yates, J. R. III, *Mol. Cell. Proteomics* 2006, 5, 53-56). However, improvement in the efficiency and sensitivity of a liquid chromatography column is still required. In this context, it has been known that the sensitivity of analysis based on liquid chromatography/mass spectrometry may be increased rapidly when the inner diameter of a separation column is decreased while maintaining the length thereof (Kim, M.-S., Choie, W.-S., Shin, Y. S., Yu, M. H., Lee, S.-W., *Bull. Korean Chem. Soc.* 2004, 25, 1833-1839).

In addition, in the case of a biological sample containing a significant amount of detergents and salts, an on-line desalting operation is an essential process required prior to mass spectrometry. This is because such impurities interrupt ionization of the peptide sample to be analyzed, resulting in a drop in detection sensitivity for the peptide sample analysis. Thus, considering time saving and sample loss, on-line desalting is more efficient than off-line desalting. Further, when a capillary column having a large length and a small inner diameter is packed with hydrophobic material, a long period of time is required to accomplish equilibrium (or regeneration) of the column. For example, at least two hours is required for such equilibrium so that a column having a length of 1 m and an inner diameter of 75 μm may be reutilized.

Meanwhile, existing liquid chromatography devices have no solid phase extraction column, and thus require a long time for sample loading. Otherwise, even when such devices use a solid phase extraction column, their resolution is poor because the sample injecting direction is the same as the sample eluting direction.

In addition, existing liquid chromatography devices use an additional valve and/or pump in order to allow the sample injecting direction and the sample eluting direction to be opposite to each other (so-called back flushing). However, this approach makes the operation of a liquid chromatography device more complex and increases the possibility of malfunctioning of the device.

SUMMARY

An embodiment of the present disclosure is directed to providing a liquid chromatography device that enables back flushing with no additional valve or pump by modifying the flow of a solvent through the use of a solvent dividing unit, thereby improving resolution.

In one general aspect, there is provided a liquid chromatography device, including:

a sample inlet valve to which a sample to be analyzed is introduced, the sample inlet valve including a sample inlet port, a sample outlet port, a first sample storage loop-connecting port and a second sample storage loop-connecting port linked to each other by a sample storage loop, a solvent inlet port, and a solvent outlet port;

a trap valve fluidically communicated with a solid phase extraction column and a reverse phase liquid chromatography column, the trap valve including a solid phase extraction column-connecting port, a reverse phase liquid chromatography column-connecting port, a first solvent inlet port, a second solvent inlet port, a sample conveying loop-connecting port linked to the solid phase extraction column-connecting port by a sample conveying loop, and a solvent outlet port; and a solvent dividing unit dividing the flow of a solvent discharged from the sample inlet valve into the first solvent inlet port and the second solvent inlet port of the trap valve.

The solvent outlet port of the sample inlet valve and the solvent dividing unit may be fluidically communicated with each other.

The liquid chromatography device may further include a solvent feed pump fluidically communicated with the solvent inlet port of the sample inlet valve to supply the solvent to the sample inlet valve.

In another general aspect, there is provided a liquid chromatography device, including:

a sample inlet valve to which a sample to be analyzed is introduced, the sample inlet valve including a sample inlet port, a sample outlet port, a first sample storage loop-connecting port and a second sample storage loop-connecting port linked to each other by a sample storage loop, a solvent inlet port, and a solvent outlet port;

a trap valve fluidically communicated with a solid phase extraction column and a reverse phase liquid chromatography column, the trap valve including a solid phase extraction column-connecting port, a reverse phase liquid chromatography column-connecting port, a first solvent inlet port, a second solvent inlet port, a sample conveying loop-connecting port linked to the solid phase extraction column-connecting port by a sample conveying loop, and a solvent outlet port; and a solvent dividing unit dividing the flow of a solvent supplied thereto into the sample inlet valve and the trap valve.

The solvent dividing unit may be fluidically communicated with the solvent inlet port of the sample inlet valve and with the second solvent inlet port of the trap valve, and the solvent outlet port of the sample inlet valve may be fluidically communicated with the first solvent inlet port of the trap valve.

The liquid chromatography device may further include a solvent feed pump fluidically communicated with the solvent dividing unit to supply the solvent to at least one of the sample inlet valve and the trap valve.

The solvent dividing unit may include a T-shaped solvent dividing tube.

In the trap valve, a Z-shaped solvent flow path may be formed between the ports fluidically communicated with each other.

The sample inlet valve may include: a first mode in which the sample inlet port is fluidically communicated with the first sample storage loop-connecting port, the second sample storage loop-connecting port is fluidically communicated with the sample outlet port, and the solvent inlet port is fluidically communicated with the solvent outlet port; and a second mode in which the sample inlet port is fluidically communicated with the sample outlet port, the first sample storage loop-connecting port is fluidically communicated with the solvent inlet port, and the second sample storage loop-connecting port is fluidically communicated with the solvent outlet port, while the trap valve may include: a first mode in which the solid phase extraction column-connecting port is fluidically communicated with the first solvent inlet port, and the sample conveying loop-connecting port is fluidically communicated with the solvent outlet port; and a second mode in which the reverse phase liquid chromatography column-connecting port is fluidically communicated with the solid phase extraction column-connecting port, and the second solvent inlet port is fluidically communicated with the sample conveying loop-connecting loop.

When the sample inlet valve is in the first mode and the trap valve is in the first mode, the sample may be loaded to the sample storage loop.

When the sample inlet valve is in the second mode and the trap valve is in the first mode, the sample may be injected to the sold-phase extraction column through the solvent.

When the sample inlet valve is in the first mode and the trap valve is in the second mode, the sample injected to the solid phase extraction column through the solvent may be introduced into the reverse phase liquid chromatography column.

The direction of the sample injected to the solid phase extraction column when the sample inlet valve is in the second mode and the trap valve is in the first mode and the direction of the sample eluted through the solid phase extraction column when the sample inlet valve is in the first mode and the trap valve is in the second mode may be opposite to each other.

The solvent feed pump may supply the solvent under a pressure of 5,000 psi to 20,000 psi.

A solvent selection valve may be disposed in the solvent feed pump so as to supply either a first solvent or a mixed solvent of a first solvent with a second solvent.

The reverse phase liquid chromatography column may be connected to a mass spectrometer.

Other features and aspects will be apparent from the following detailed description and the claims.

BRIEF DESCRIPTION OF THE DRAWINGS

The above and other aspects, features and advantages of the disclosed exemplary embodiments will be more apparent from the following detailed description taken in conjunction with the accompanying drawings in which.

DETAILED DESCRIPTION OF EMBODIMENTS

The advantages, features and aspects of the present disclosure will become apparent from the following description of the embodiments with reference to the accompanying drawings, which is set forth hereinafter. The present disclosure may, however, be embodied in different forms and should not be construed as limited to the embodiments set forth herein. Rather, these embodiments are provided so that this disclosure will be thorough and complete, and will fully convey the scope of the present disclosure to those skilled in the art. The terminology used herein is for the purpose of describing particular embodiments only and is not intended to be limiting of example embodiments. As used herein, the singular forms "a", "an" and "the" are intended to include the plural forms as well, unless the context clearly indicates otherwise. It will be further understood that the terms "comprises" and/or "comprising", when used in this specification, specify the presence of stated features, integers, steps, operations, elements, and/or components, but do not preclude the presence or addition of one or more other features, integers, steps, operations, elements, components, and/or groups thereof.

Figure 1A:
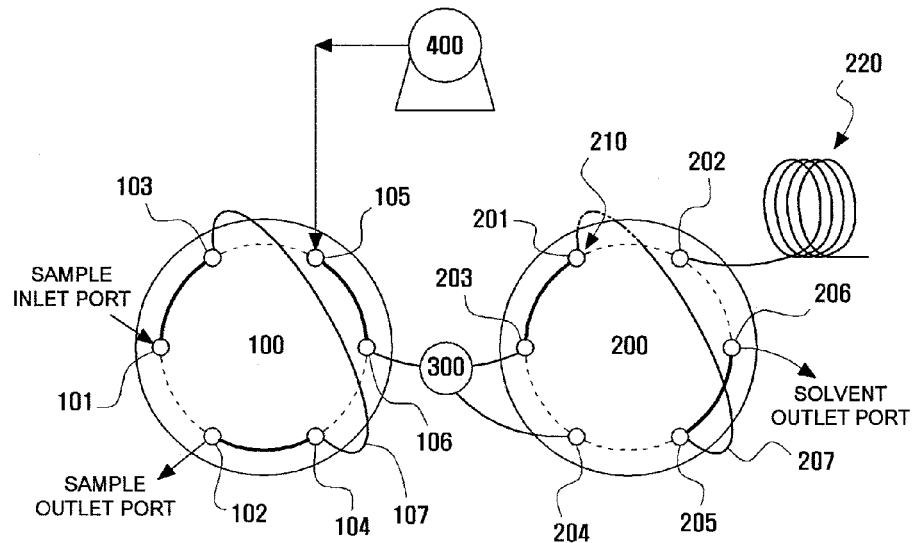
FIG. 1a is a schematic view showing the valve configuration in a sample loading mode of the liquid chromatography device according to one embodiment.

In one aspect, there is provided a liquid chromatography device. As shown in FIG. 1a, the liquid chromatography device includes:

a sample inlet valve 100 including a sample inlet port 101, a sample outlet port 102, a first sample storage loop-connecting port 103 and a second sample storage loop-connecting port 104 linked to each other by a sample storage loop 107, a solvent inlet port 105, and a solvent outlet port 106;

a trap valve 200 fluidically communicated with a solid phase extraction column 210 and a reverse phase liquid chromatography column 220, the trap valve including a solid phase extraction column-connecting port 201, a reverse phase liquid chromatography column-connecting port 202, a first solvent inlet port 203, a second solvent inlet port 204, a sample conveying loop-connecting port 205 linked to the solid phase extraction column-connecting port by a sample conveying loop 207, and a solvent outlet port 206; and a solvent dividing unit 300 dividing the flow of a solvent discharged from the sample inlet valve 100 into the first solvent inlet port 203 and the second solvent inlet port 204 of the trap valve 200.

Figure 1B:
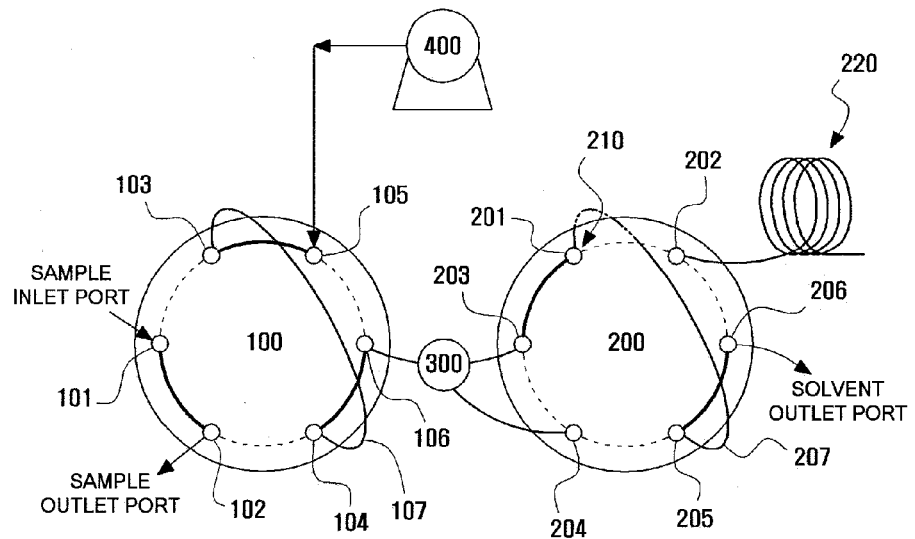
FIG. 1b is a schematic view showing the valve configuration in a sample injecting mode of the liquid chromatography device according to one embodiment.
Figure 1C:
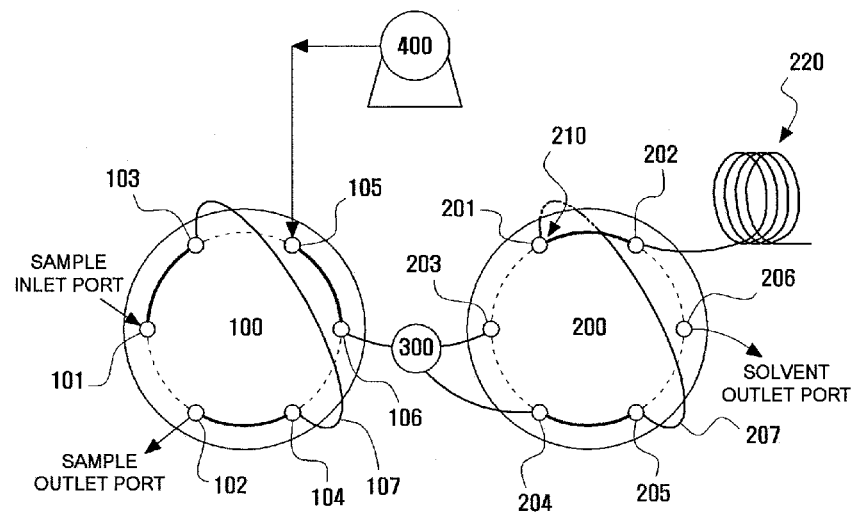
FIG. 1c is a schematic view showing the valve configuration in a sample separating mode of the liquid chromatography device according to one embodiment.

The liquid chromatography device is operated in three modes, including a sample loading mode, a sample injecting mode and a sample separating mode. FIGS. 1a to 1c show the configuration of the sample inlet valve 100 and the trap valve 200 in each mode.

As shown in FIG. 1a, the liquid chromatography device disclosed herein includes two valves, i.e., a sample inlet valve 100 and a trap valve 200.

The sample inlet valve 100 receives a sample introduced thereto and includes six ports, including a sample inlet port 101, a sample outlet port 102, a first sample storage loop-connecting port 103, a second sample storage loop-connecting port 104, a solvent inlet port 105 and a solvent outlet port 106.

In a sample loading mode, a sample to be analyzed is introduced through the sample inlet port 101. The sample introduced through the sample inlet port 101 is linked to a sample storage loop 107 having a predetermined volume. The sample storage loop 107 allows the users to obtain a sufficient sample concentration by repeating sample injection many times if a given sample concentration is judged to be too low.

The sample storage loop 107 may have a volume of 1 µL to 10 µL. When the sample storage loop 107 has a volume less than 1 µL, sample handling may be difficult. On the other hand, when the sample storage loop has a volume greater than 10 µL, it takes too long time to inject a sample.

In addition, the sample inlet valve 100 includes a sample outlet port 102, which allows discharge of an excessive amount of sample so that the sample storage loop 107 may receive the sample in the above-specified range of volumes.

After completing the sample introduction as described above, a mode switch (not shown) of the sample inlet valve 100 is used to convert the operating mode from a first mode to a second mode, so that the configuration of the ports is converted from a sample loading mode (FIG. 1a) into a sample injecting mode (FIG. 1b).

The liquid chromatography device according to one embodiment may further include a solvent feed pump 400 fluidically communicated with the solvent inlet port 105 of the sample inlet valve 100 to supply a solvent to the sample inlet valve 100.

The solvent feed pump 400 may supply the solvent under a pressure of 5,000 psi to 20,000 psi. When the pressure is lower than 5,000 psi, resolution may be degraded because the available length of a column is decreased. On the other hand, when the pressure is higher than 20,000 psi, the solvent may be leaked from the valve.

The solvent supplied from the solvent feed pump 400 may be a first solvent or a mixed solvent of a first solvent with a second solvent. For this, the solvent feed pump 400 is provided with a solvent selection valve (not shown) to supply either the first solvent or the mixed solvent containing the first solvent and the second solvent in a predetermined ratio.

In the sample injecting mode, the first solvent is introduced from the solvent feed pump 400 through solvent inlet port 105. Then, the sample retained in the sample storage loop 107 is passed through the solvent dividing unit 300 via the solvent outlet port 106 by the hydraulic pressure of the first solvent.

Particularly, the liquid chromatography device according to one embodiment is characterized in that the sample and the solvent passed through the solvent dividing unit 300 are divided into two solvent inlet ports 203, 204, and then introduced into the trap valve 200.

The solvent dividing unit 300 may include a T-shaped solvent dividing tube to divide the fluid introduced thereto into two branches.

The trap valve 200 includes a solid phase extraction column-connecting port 201, a reverse phase liquid chromatography column-connecting port 202, a first solvent inlet port 203, a second solvent inlet port 204, a sample conveying loop-connecting port 205 and a solvent outlet port 206.

As shown in FIG. 1b illustrating the configuration of the trap valve in a sample injecting mode, the solid phase extraction column-connecting port 201 is fluidically communicated with the first solvent inlet port 203, and the sample conveying loop-connecting port 205 is fluidically communicated with the solvent outlet port 206.

Therefore, the sample conveyed with the first solvent from the sample inlet valve 100 is passed through the solvent dividing unit 300, and then sent to the solid phase extraction column 210 through the solid phase extraction column-connecting port 201 by way of the first solvent inlet port 203.

As shown in FIGS. 1a to 1c, the trap valve 200 may be provided with a Z-shaped solvent flow path between the ports fluidically communicated with each other. For example, as shown in FIG. 1b, a Z-shaped solvent flow path is formed by the first solvent inlet port 203, the solid phase extraction column-connecting port 201 and the sample conveying loop 207, fluidically communicated with one another, as well as by the sample conveying loop-connecting port 205 and the solvent outlet port 206 fluidically communicated with each other.

The solid phase extraction column 210 is connected directly to the solid phase extraction column-connecting port 201. The solid phase extraction column 210 has an inner diameter of 50 µm to 500 µm and a length of 1 cm to 4 cm. Such a length is significantly smaller than the conventional solid phase extraction columns. Since the solid phase extraction column has such a small length even though it is operated under a very high pressure of about 20,000 psi, it is possible to maximize the resolution upon separating a sample. In addition, as described hereinafter, it is possible to further improve the resolution due to the so-called back flushing.

According to one embodiment, a stainless steel liner of an internal reducer is used as a solid phase extraction column 210, and a material, such as a C18 material, is packed into the column. Then, both ends of the column are closed with stainless steel screens having a pore size of about 2 µm to prevent the packing material from being discharged from the column. In this manner, a firm solid phase extraction column that may resist against such a high pressure is provided.

Meanwhile, the flow rate of the sample introduced into the solid phase extraction column 210 by the hydraulic pressure of the first solvent may be controlled through the solvent outlet port 206. The solvent outlet port 206 discharges the first solvent at a flow rate of 0.5 µL/min to 10 µL/min, thereby controlling the flow rate of the sample supplied to the solid phase extraction column 210. In addition, the solvent outlet port 206 discharges the salt contents contained in the sample, thereby accomplishing efficient desalting.

While the sample is subjected to desalting in the above-described manner, the flow rate of the sample in the solid phase extraction column may be controlled in a range between 1.8 µL/min and 2.0 µL/min.

The reasons why the flow rate of the sample in the solid phase extraction column is controlled in a range between 1.8 µL/min and 2.0 µL/min are to increase the desalting efficiency, to prevent an increase in the resultant internal pressure and to ensure minimization of sample loss in the solid phase extraction column.

Hereinabove, described is a process including supplying a predetermined amount of sample to the sample storage loop 107 through the sample inlet port 101, and passing the sample through the solvent dividing unit 300 by the first solvent and then injecting it to the solid phase extraction column 210.

Next, separation of the sample injected to the solid phase extraction column 210 using a second solvent is to be carried out. This will be described hereinafter in detail. Particularly, it is to be noted that the liquid chromatography device disclosed herein realizes improved resolution by allowing the sample injecting direction and the sample eluting direction to be opposite to each other (so-called back flushing) through the use of the solvent dividing unit 300.

FIG. 1c shows the sample inlet valve 100 and the trap valve 200 converted into a configuration corresponding to a sample separating mode. Referring to FIG. 1c, in the sample separating mode, the sample inlet valve 100 shows a configuration wherein the solvent inlet port 105 is fluidically communicated with the solvent outlet port 106, so that the solvent supplied from the solvent feed pump 400 is passed through the solvent dividing unit 300 by way of the two ports. For this, a mode switch of the sample inlet valve 100 is used to convert each of the ports from the second mode (FIG. 1b) to the first mode (FIG. 1c).

The solvent used in the sample separating mode is a mixed solvent of the first solvent with the second solvent. By varying the mixing ratio of the two solvents, it is possible to separate the sample through a solvent gradient.

In addition, in the sample separating mode, the trap valve 200 shows a configuration wherein the second solvent inlet port 204 is fluidically communicated with the sample conveying loop-connecting port 205, and the solid phase extraction column-connecting port 201 is fluidically communicated with the reverse phase liquid chromatography column-connecting port 202. Therefore, the mixed solvent passed through the solvent dividing unit 300 is conveyed to the solid phase extraction column 210 by way of the sample conveying loop 207. For this, a mode switch of the trap valve 200 is used to convert each of the ports from the first mode (FIG. 1b) to the second mode (FIG. 1c).

Therefore, according to one embodiment of the liquid chromatography device disclosed herein, it is possible to accomplish the so-called back flushing by using the trap valve 200 having two solvent inlet valves in combination with the solvent dividing unit 300 without any additional valve and additional solvent feed pump.

Separation of the sample in the solid phase extraction column 210 is carried out while varying the ratio of the first solvent to the second solvent of the mixed solvent supplied from the solvent feed pump 400 with time. In other words, as the proportion of the second solvent in the mixed solvent increases, the degree of detachment of the sample attached to the solid phase extraction column 210 increases, and the sample having such an increased detachment degree is introduced to the reverse phase liquid chromatography column 220 and then is separated.

Various combinations of the first solvent with the second solvent may be used to accomplish the above-described purpose. As a non-limiting example, 0.1% aqueous formic acid solution and 90% aqueous acetonitrile solution may be used as the first solvent and the second solvent, respectively. In brief, such selection of solvents depends on the fact that a higher proportion of acetonitrile in the mixed solvent results in a higher degree of detachment of the sample attached to the solid phase extraction column.

The reverse phase liquid chromatography column 220 in which the sample is separated may have an inner diameter of 15 μm to 150 μm and a length of 10 cm to 150 cm. The reverse phase liquid chromatography column 220 is connected to a mass spectrometer for the purpose of subsequent analysis.

Figure 2A:
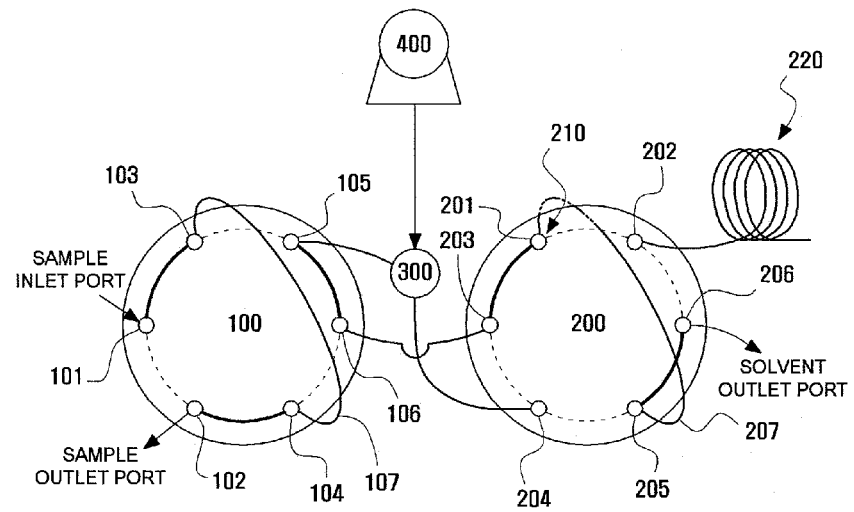
FIG. 2a is a schematic view showing the valve configuration in a sample loading mode of the liquid chromatography device according to another embodiment.

In another aspect, there is provided a liquid chromatography device. As shown in FIG. 2a, the liquid chromatography device includes:

a sample inlet valve 100 to which a sample to be analyzed is introduced, the sample inlet valve including a sample inlet port 101, a sample outlet port 102, a first sample storage loop-connecting port 103 and a second sample storage loop-connecting port 104 linked to each other by a sample storage loop 107, a solvent inlet port 105, and a solvent outlet port 106;

a trap valve 200 fluidically communicated with a solid phase extraction column 210 and a reverse phase liquid chromatography column 220, the trap valve including a solid phase extraction column-connecting port 201, a reverse phase liquid chromatography column-connecting port 202, a first solvent inlet port 203, a second solvent inlet port 204, a sample conveying loop-connecting port 205 linked to the solid phase extraction column-connecting port by a sample conveying loop 207, and a solvent outlet port 206; and a solvent dividing unit 300 dividing the flow of a solvent supplied thereto into the sample inlet valve 100 and the trap valve 200.

The solvent dividing unit 300 is fluidically communicated with the solvent inlet port 105 of the sample inlet valve 100 and the second solvent inlet port 204 of the trap valve 200. In addition, the solvent outlet port 106 of the sample inlet valve 100 is fluidically communicated with the first solvent inlet port 203 of the trap valve 200.

In this case, the liquid chromatography device may further include a solvent feed pump 400 communicated with the inlet side of the solvent dividing unit 300 to supply the solvent to at least one valve of the sample inlet valve 100 and the trap valve 200.

FIG. 2a shows a configuration of the sample inlet valve 100 and the trap valve 200 in a sample loading mode. The liquid chromatography device as shown in FIG. 2a is different from the device as shown in FIG. 1a only in that the solvent supplied from the solvent feed pump 400 is introduced directly to the solvent dividing unit 300, and then the flow of the solvent is divided into the solvent inlet port 105 of the sample inlet valve 100 and the second solvent inlet port 204 of the trap valve 200 by the solvent dividing unit 300. The other features, including the flow of sample and the flow of solvent in a sample loading mode, a sample injecting mode and a sample separating mode, are the same.

Figure 2B:
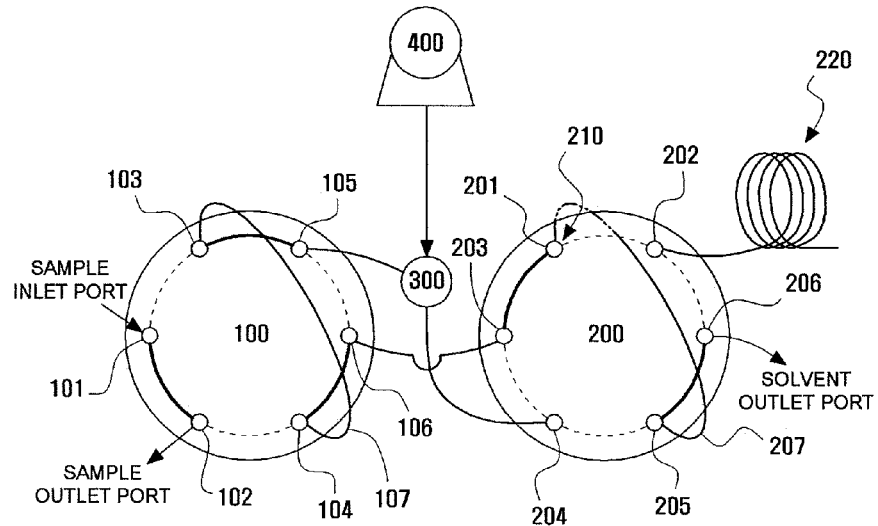
FIG. 2b is a schematic view showing the valve configuration in a sample injecting mode of the liquid chromatography device according to another embodiment.
Figure 2C:
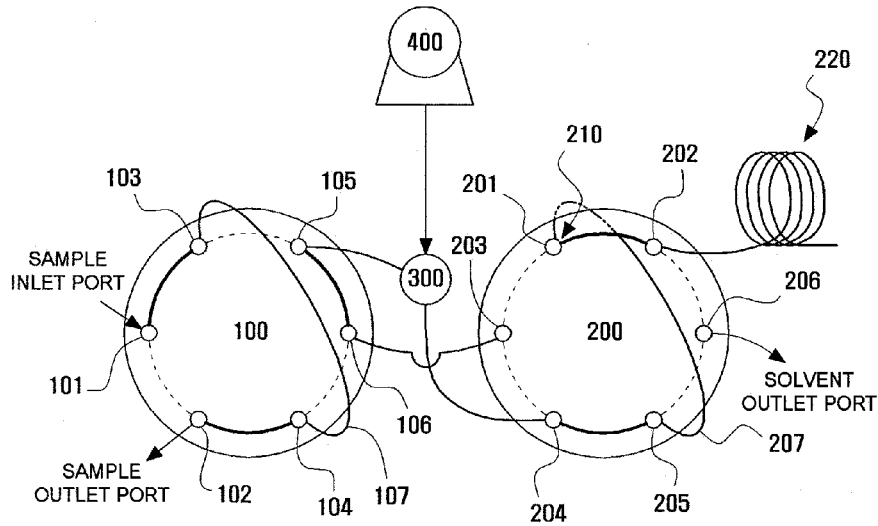
FIG. 2c is a schematic view showing the valve configuration in a sample separating mode of the liquid chromatography device according to another embodiment.

In other words, the trap valve 200 as shown in FIGS. 2a to 2c has a Z-shaped solvent flow path between the ports fluidically communicated with each other.

FIGS. 2b and 2c show the configuration of the sample inlet valve 100 and the trap valve 200 in a sample injecting mode and in a sample separating mode of the liquid chromatography device according to another embodiment, respectively.

As shown in FIGS. 2a to 2c, the liquid chromatography device according to another embodiment also accomplishes the so-called back flushing by using the trap valve 200 having two solvent inlet valves in combination with the solvent dividing unit 300 without any additional valve and additional solvent feed pump.

EXAMPLES

The examples and experiments will now be described. The following examples and experiments are for illustrative purposes only and not intended to limit the scope of this disclosure.

Pretreatment of Sample

As a sample to be analyzed, enolase isolated from bakers yeast (available from Sigma-Aldrich, St. Louis, Mo., USA) is used. The sample is pretreated by using Sequencing Grade Modified Porcine Trypsin (Promega, Madison, Wis., USA). The sample is pretreated as follows.

First, enolase is dissolved into 100 mM $NH_4HCO_3$ buffer and modified thermally at 90° C. for 10 minutes, followed by cooling to room temperature. Next, methanol is added thereto and trypsin is further added in such an amount that the weight ratio of the substrate to enzyme is 50:1. The trypsin-induced hydrolysis is carried out at 37° C. for 12 hours.

Meanwhile, to perform an analysis of more complicated proteome samples, trypsin-decomposed peptides of whole lysate of yeast are used. The yeast proteomes used herein are haploid strains of S. cerevisiae, Y 2805 (MATa pep::his3 prb1-D1.6R can1 his1-200 ura3-52) and AF-2 (HMLa or HMRa ho ade2-1 trp1-1 can1-100 leu2-3,112 his3-11,15 ura3-1 ssd1) (Kim, M.-S., Choie, W.-S., Shin, Y. S., Yu, M. H., Lee, S.-W., *Bull. Korean Chem. Soc.* 2004, 25, 1833-1839). In this case, the proteins are dissolved into 100 mM $NH_4HCO_3$ buffer, trypsin is added thereto, and hydrolysis is carried out at 37° C. for 12 hours. The resultant products are dried completely by using SPeedVac system (SPD1010; ThermoSavant, Holbrook, N.Y., USA), and then stored at −20° C. for the subsequent experiment.

Instruments

As a first solvent, 0.1% aqueous formic acid solution (available from Merck (Darmstadt, Germany)) is used. In addition, 100% acetonitrile containing 0.1% formic acid (available from J. T. Baker (Phillipsburg, N.J., USA)) is used as a second solvent.

A capillary column (reverse phase liquid chromatography column) (75 μm ID×360 μm OD×80 cm length) is made by packing a fused silica capillary with slurry of C18-bound particles (Shen, Y., Moore, R. J., Zhao, R., Blonder, J., et al., *Anal. Chem.* 2003, 75, 3596-3605; Shen, Y., Tolic N., Masselon, C., Pasa-Tolic L. et al., *Anal. Chem.* 2004, 76, 144-154; Shen, Y., Smith, R. D., Unger K. K., Kumar, D., Lubda, D., *Anal. Chem.* 2005, 77, 6692-6701).

A solid phase extraction column is produced by using an internal reducer available from VICI (Houston, Tex., USA). More particularly, the 1 cm liner (250 μm ID) disposed in the internal reducer (1/16" to 1/32") is packed with a C18 material under a pressure of 10,000 psi. After the completion of the packing, the column is subjected to ultrasonication for 5 minutes while maintaining a pressure of 10,000 psi. The column is depressurized over night before it is used so that the C18 packing material is prevented from scattering. In addition, before the column is used for actual experiments, both ends of the liner are closed with stainless steel screens (pore size: 2 μm).

Meanwhile, the reverse phase liquid chromatography column is connected to a mass spectrometer that is 7-tesla Fourier-transform ion cyclotron resonance mass spectrometer (FTICR, LTQ-FT, ThermoFinnigan) equipped with a nanoelectrospray ionization interface.

Evaluation of Results

The liquid chromatography device according to one embodiment is used to analyze the trypsin-decomposed enolase products obtained from the above-described pretreatment.

Figure 3:
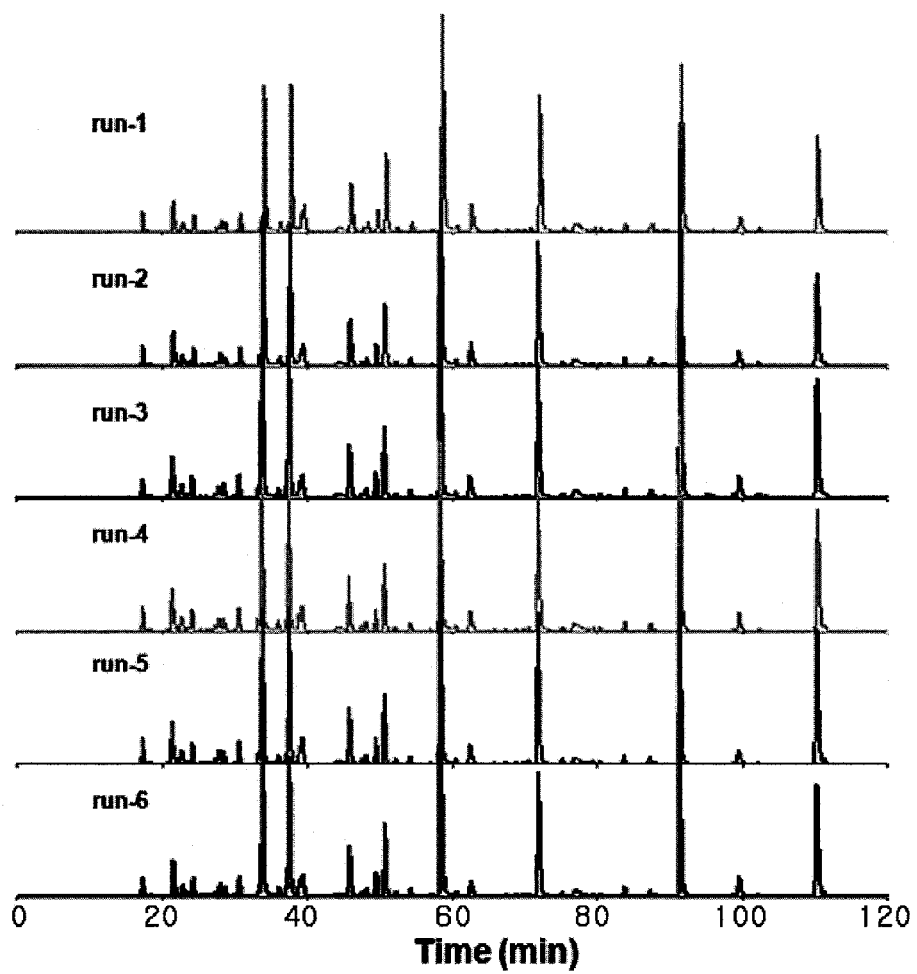
FIG. 3 is a chromatogram of the sample separated from the liquid chromatography device according to one embodiment.

The analysis is repeated six times under the same condition in order to demonstrate the reproducibility of the liquid chromatography device. After the peptide sample is sent to the solid phase extraction column, it is separated by reverse phase liquid chromatography. Thus the separated sample is detected by the mass spectrometer, and the chromatogram of the sample is shown in FIG. 3.

It is shown that a standard deviation within 0.1% is provided each time. This demonstrates that the liquid chromatography device disclosed herein has excellent reproducibility.

As can be seen from the foregoing, it is possible to provide a high-efficiency and high-reproducibility liquid chromatography device with a simple configuration. The liquid chromatography device improves resolution using specialized cooperation between a T-shaped solvent dividing unit and a trap valve provided with a Z-shaped solvent flow path to modify the flow of a solvent introduced into/discharged from the sample inlet valve and the trap valve so that the sample injecting direction and the sample eluting direction are opposite to each other. In addition, the liquid chromatography device accomplishes on-line desalting of a sample, and shows high reproducibility in liquid chromatography over the whole retention time.

While the present disclosure has been described with respect to the specific embodiments, it will be apparent to those skilled in the art that various changes and modifications may be made without departing from the spirit and scope of the disclosure as defined in the following claims.

What is claimed is:

1. A liquid chromatography device, comprising:
   a sample inlet valve to which a sample to be analyzed is introduced, the sample inlet valve including a sample inlet port, a sample outlet port, a first sample storage loop-connecting port and a second sample storage loop-connecting port linked to each other by a sample storage loop, a solvent inlet port, and a solvent outlet port;
   a trap valve fluidically communicated with a solid phase extraction column and a reverse phase liquid chromatography column, the trap valve including a solid phase extraction column-connecting port, a reverse phase liquid chromatography column-connecting port, a first solvent inlet port, a second solvent inlet port, a sample conveying loop-connecting port linked to the solid phase extraction column-connecting port by a sample conveying loop, and a solvent outlet port; and
   a solvent dividing unit dividing flow of a solvent supplied thereto into the sample inlet valve and the trap valve.

2. The liquid chromatography device according to claim 1, wherein the solvent dividing unit is fluidically communicated with the solvent inlet port of the sample inlet valve and with the second solvent inlet port of the trap valve, and the solvent outlet port of the sample inlet valve is fluidically communicated with the first solvent inlet port of the trap valve.

3. The liquid chromatography device according to claim 1, which further comprises a solvent feed pump fluidically communicated with the solvent dividing unit to supply the solvent to at least one of the sample inlet valve and the trap valve.

4. The liquid chromatography device according to claim 1, wherein the solvent dividing unit comprises a T-shaped solvent dividing tube.

5. The liquid chromatography device according to claim 1, wherein a Z-shaped solvent flow path is formed between the ports fluidically communicated with each other in the trap valve.

6. The liquid chromatography device according to claim 1, wherein the sample inlet valve comprises:
   a first mode in which the sample inlet port is fluidically communicated with the first sample storage loop-connecting port, the second sample storage loop-connecting port is fluidically communicated with the sample outlet port, and the solvent inlet port is fluidically communicated with the solvent outlet port; and a second mode in which the sample inlet port is fluidically communicated with the sample outlet port, the first sample storage loop-connecting port is fluidically communicated with the solvent inlet port, and the second sample storage loop-connecting port is fluidically communicated with the solvent outlet port, while the trap valve comprises:

the first mode in which the solid phase extraction column-connecting port is fluidically communicated with the first solvent inlet port, and the sample conveying loop-connecting port is fluidically communicated with the solvent outlet port; and the second mode in which the reverse phase liquid chromatography column-connecting port is fluidically communicated with the solid phase extraction column-connecting port, and the second solvent inlet port is fluidically communicated with the sample conveying loop-connecting loop.

7. The liquid chromatography device according to claim 6, wherein the sample is loaded to the sample storage loop when the sample inlet valve is in the first mode and the trap valve is in the first mode.

8. The liquid chromatography device according to claim 6, wherein the sample is injected to the sold-phase extraction column through the solvent when the sample inlet valve is in the second mode and the trap valve is in the first mode.

9. The liquid chromatography device according to claim 6, wherein the sample injected to the solid phase extraction column through the solvent is introduced into the reverse phase liquid chromatography column when the sample inlet valve is in the first mode and the trap valve is in the second mode.

10. The liquid chromatography device according to claim 6, wherein a direction of the sample injected to the solid phase extraction column when the sample inlet valve is in the second mode and the trap valve is in the first mode and a direction of the sample eluted through the solid phase extraction column when the sample inlet valve is in the first mode and the trap valve is in the second mode are opposite to each other.

11. The liquid chromatography device according to claim 3, wherein the solvent feed pump supplies the solvent under a pressure of 5,000 psi to 20,000 psi.

12. The liquid chromatography device according to claim 3, wherein a solvent selection valve is disposed in the solvent feed pump so as to supply either a first solvent or a mixed solvent of the first solvent with a second solvent.

13. The liquid chromatography device according to claim 1, wherein the reverse phase liquid chromatography column is connected to a mass spectrometer.

* * * * *